United States Patent
Ino et al.

(10) Patent No.: US 12,105,080 B2
(45) Date of Patent: Oct. 1, 2024

(54) ELECTROCHEMICAL MEASUREMENT APPARATUS AND TRANSDUCER

(71) Applicants: TOHOKU UNIVERSITY, Miyagi (JP); JAPAN AVIATION ELECTRONICS INDUSTRY, LIMITED, Tokyo (JP)

(72) Inventors: Kosuke Ino, Miyagi (JP); Yusuke Kanno, Miyagi (JP); Tomokazu Matsue, Miyagi (JP); Kumi Inoue, Miyagi (JP); Ryota Kunikata, Tokyo (JP); Hiroyuki Hayashi, Tokyo (JP); Atsushi Suda, Tokyo (JP)

(73) Assignees: TOHOKU UNIVERSITY, Miyagi (JP); JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 0 days.

(21) Appl. No.: 17/027,172

(22) Filed: Sep. 21, 2020

(65) Prior Publication Data

US 2021/0003549 A1  Jan. 7, 2021

Related U.S. Application Data

(62) Division of application No. 15/597,454, filed on May 17, 2017, now abandoned.

(30) Foreign Application Priority Data

May 20, 2016  (JP) .................................. 2016-101043

(51) Int. Cl.
*G01N 33/487*  (2006.01)
*G01N 27/327*  (2006.01)
(Continued)

(52) U.S. Cl.
CPC ... *G01N 33/48735* (2013.01); *G01N 27/3271* (2013.01); *G01N 27/4161* (2013.01);
(Continued)

(58) Field of Classification Search
CPC ......... G01N 33/48735; G01N 27/3271; G01N 27/4161; G01N 33/5005;
(Continued)

(56) References Cited

U.S. PATENT DOCUMENTS

| 8,669,771 B2* | 3/2014 | Trumper | ................ B82Y 35/00 |
| | | | 324/683 |
| 2013/0053268 A1* | 2/2013 | Frederix | .............. C12Q 1/6825 |
| | | | 506/18 |
| 2014/0197851 A1* | 7/2014 | Astley | ................ G01N 33/0006 |
| | | | 324/660 |

FOREIGN PATENT DOCUMENTS

| EP | 823483 A1 * | 2/1998 | ............ C12M 21/08 |
| EP | 1278064 | 1/2003 | |

(Continued)

OTHER PUBLICATIONS

Inoue et al. (KY Inoue, et al., Advanced LSI-based amperometric sensor array with light-shielding structure for effective removal of photocurrent and mode selectable function for individual operation of 400 electrodes, Lab Chip, 15 (2015) 848 (Year: 2014).*
(Continued)

*Primary Examiner* — Luan V Van
*Assistant Examiner* — Shizhi Qian
(74) *Attorney, Agent, or Firm* — GREENBLUM & BERNSTEIN P.L.C.

(57) ABSTRACT

An electrochemical measurement apparatus includes: a tank containing electrolytic solution and a sample that generates or consumes measurement target substances in the electrolytic solution; a plurality of uniformly mixed working elec-
(Continued)

trodes; and a counter electrode; the apparatus adapted to simultaneously apply a voltage between each of the working electrodes and the counter electrode; and the apparatus configured to measure a current that flows between each of the working electrodes and the counter electrode; wherein any two working electrode groups are mutually different in at least any of the determined voltage, presence/absence of a molecular modification of an electrode surface, and a species of the molecular modification; and whereby a distribution in measurement area of the currents that flow through the working electrodes is acquired.

6 Claims, 11 Drawing Sheets

(51) Int. Cl.
| | | |
|---|---|---|
| *G01N 27/416* | (2006.01) | |
| *G01N 33/50* | (2006.01) | |
| *G06T 7/00* | (2017.01) | |
| *G06T 7/90* | (2017.01) | |

(52) U.S. Cl.
CPC ....... *G01N 33/5005* (2013.01); *G06T 7/0012* (2013.01); *G06T 7/90* (2017.01); *G06T 2207/10016* (2013.01)

(58) Field of Classification Search
CPC .... G01N 33/0004–0075; G06T 7/0012; G06T 7/90; G06T 2207/10016
See application file for complete search history.

(56) References Cited

FOREIGN PATENT DOCUMENTS

| | | |
|---|---|---|
| JP | 2010-014558 | 1/2010 |
| JP | 2013-057617 | 3/2013 |
| JP | 2013-092437 A | 5/2013 |

OTHER PUBLICATIONS

Sen et al., "LSI-based amperometric sensor for real-time monitoring of embryoid bodies," Biosensors and Bioelectronics, Elsevier B.V., Dec. 18, 2013, pp. 1-7.

Ino et al., "Colorization of Electrochemical Bioimaging using a Large-Scale Integration Device", The 96th CSJ Annual Meeting, Mar. 10, 2016, p. 1.

Kanno et al., "Multicolor Electrochemical Imaging for Simultaneous Multiple Analysis of Neuron-like Cell Aggregates", The 96th CSJ Annual Meeting, Mar. 23, 2016, pp. 1, English translation.

Kanno et al., "Coloring of Electrochemical Imaging by LSI Electrode Array ," Proceedings of the 76th Discussion Meeting of Analytical Chemistry, published May 14, 2016, p. 29.

Kanno et al., "Feedback mode-based electrochemical imaging . . . " Electroanalytical Chem., vol. 741, 2015, pp. 109-113.

Kanno et al., "Potentiometric imaging of stem cells using an LSI-Based electrochemical chip device with 400 microelectrodes," 19th Int'l Conference on Miniaturized System for Chemistry and Life Sciences, Oct. 25, 2017, p. 1686.

JP Office Action in JP Patent Application No. 2016-101043, Sep. 26, 2017, English translation.

Inoue et al. "Advanced LSI-based amperometric sensor array with light-shielding structure for effective removal of photocurrent and mode selectable function for individual operation of 400 electrodes," Lab Chip, 15(2015) 948 (2014).

Abe et al. "Electrochemical Imaging of Dopamine Release from Three-Dimensional-Cultured PC12 Cells Using Large-Scale Integration-Based Amperometric Sensors," Anal. Chem. 87 (2015) 6364-6370.

Bellin et al. "Electrochemical camera chip for simultaneous imaging of multiple metabolites in biofilms," Nat. Commun. 7 (2016) 10535.

Hayashi et al. "Real-time electrochemical imaging using an individually addressable multichannel electrode," Biosensors and Bioelectronics 15 (2000) 523-529.

Ino et al. Addressable electrode array device with IDS electrodes for high-throughput detection, 11 (2011) 385-388.

Ino et al. "Local redox-cycling between vertically separated electrodes in substrate generation/chip collection and extended feedback modes" Anal. Chem. 86 (2014) 4016-4023.

Ino et al. "Local redox-cycling-based electrochemical ship device with deep microwells for evaluation of embryoid bodies" Angew. Chem. Int. Ed. 51 (2012) 6648-6652.

Kuno et al. "Amperometric electrochemical sensor array for on-chip simultaneous imaging" Jpn. J. Appl. Phys. 53 (2014) 04EL01-1 through 04EL01-7.

Laborde et al., "Real-time imaging of microparticles and living cells with CMOS nanocapacitor arrays" Nature nanotech 10(2-15) 791-796, 2015.

Schienle et al. "A fully electronic DNA sensor with 128 positions and in-pixel A/D conversion" IEEE Journal of Solid-State Circuits 39(12)(2004) 2438-2445.

\* cited by examiner

DETECTION OF DISSOLVED OXYGEN

DETECTION OF DOPAMINE

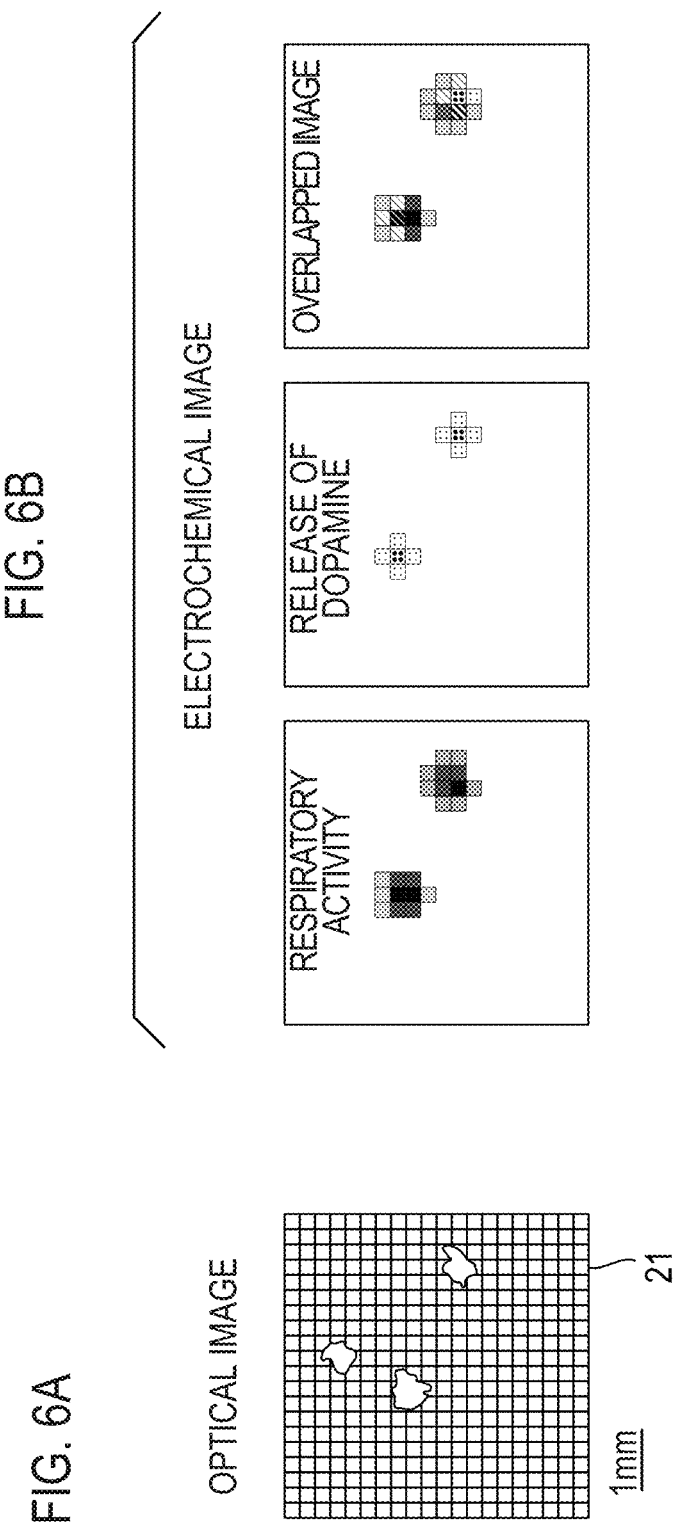

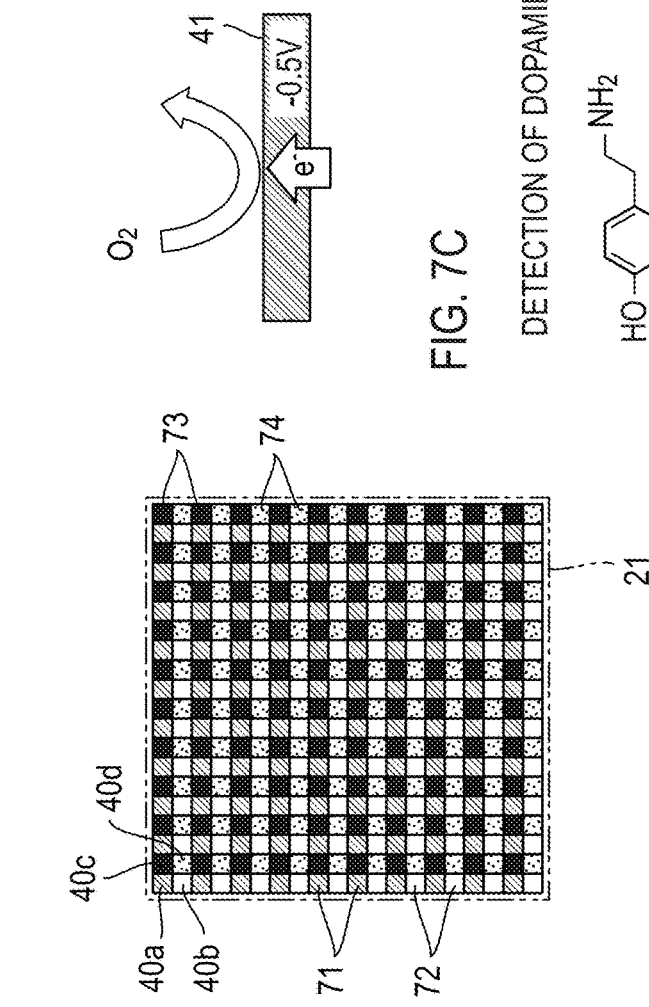
FIG. 7A
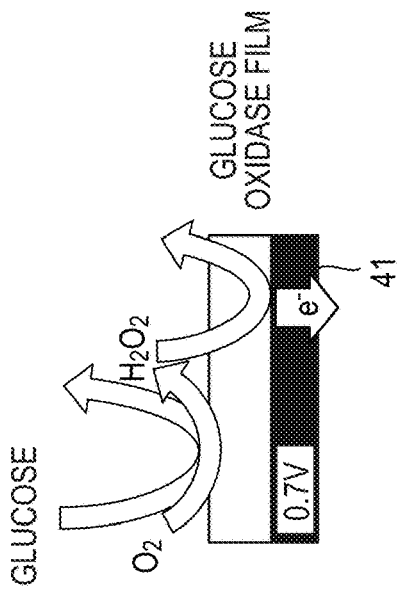
FIG. 7B
DETECTION OF DISSOLVED OXYGEN
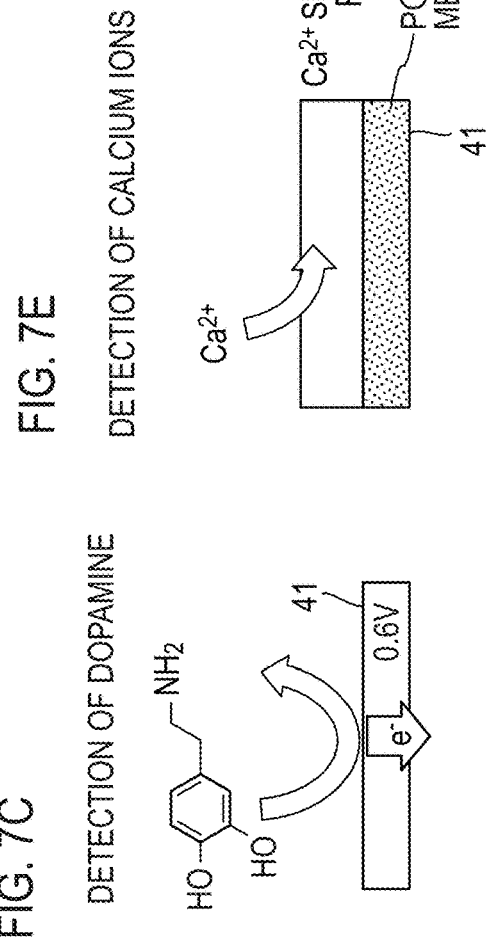
FIG. 7D
DETECTION OF GLUCOSE
FIG. 7C
DETECTION OF DOPAMINE
FIG. 7E
DETECTION OF CALCIUM IONS

DETECTION OF DOPAMINE

DETECTION OF DISSOLVED OXYGEN

ELECTROCHEMICAL MEASUREMENT APPARATUS AND TRANSDUCER

This application is a Divisional of U.S. application Ser. No. 15/597,454, filed May 17, 2017, which claims priority to JP Application No. JP 2016-101043, filed May 20, 2016. The disclosure of each of these applications is herein incorporated by reference in its entirety.

TECHNICAL FIELD

The present invention relates to measurement of chemical substances derived from a biological sample, such as cells, a cell aggregate and a tissue piece, and a non-biological sample that comprises bio-related substances (hereinafter generically and simply referred to as "a biological sample"), and in particular to an electrochemical imaging method enabling measurement of distributions of a plurality of kinds of chemical substances in a measurement area and acquisition of images of the distributions, an electrochemical measurement apparatus and a transducer used for electrochemical measurement.

BACKGROUND ART

To quantitate substances generated by a chemical reaction that occurs in a biological sample such as cells, a cell aggregate and a tissue piece is an important technique for life-death determination, functionality evaluation and the like of the biological sample in the medical field, drug development field and the like. One of methods for quantitating a chemical reaction product released from a biological sample is electrochemical measurement.

Electrochemical measurement by current measurement is a method of acquiring a current value from an electrode by taking away electrons from a measurement target substance in an electrolytic solution (an oxidation reaction) or giving electrons to the measurement target substance (a reduction reaction) via the electrode to detect whether a redox reaction on the electrode has occurred or not, that is, whether the measurement target substance exists or not.

Such an electrochemical method by current measurement is widely used. In order to perform exhaustive analysis and imaging, however, it is necessary to arrange a lot of sensor electrodes (working electrodes). For example, in "Biosensors and Bioelectronics" by M. Sen, et al., 2013, Volume 48, p. 12-18 (hereinafter referred to as Literature 1), ø50 µm working electrodes, the number of which is 20×20=400, are arranged at the pitch of 250 µm, and exhaustive analysis and imaging of a biological sample are performed with a current value obtained from the 400 working electrodes arranged in an array.

On the other hand, in Japanese Patent Application Laid Open No. 2013-092437 (published on May 16, 2013; hereinafter referred to as Literature 2), an IC chip used for electrochemical measurement is described. This IC chip has working electrodes arranged in an array, and it is possible to switch among measurement modes by a group of switches provided for the working electrodes. For example, it is possible to select a current/voltage conversion measurement mode for measuring a current that flows when a working electrode is set to a predetermined electric potential, an offset current/voltage conversion measurement mode for measuring a current that flows through a working electrode when the working electrode is set to an electric potential offset from the predetermined electric potential, and the like.

By using the IC chip described in Literature 2 described above, it is possible to simultaneously measure two kinds of measurement target substances with different redox potentials. In Literature 2, however, a specific method for simultaneously imaging two kinds of measurement target substances is not described.

SUMMARY OF THE INVENTION

An object of the present invention is to provide an electrochemical imaging method for simultaneously imaging density distributions of a plurality of kinds of measurement target substances in a measurement area and further provide an electrochemical measurement apparatus and a transducer used for the electrochemical imaging.

According to an electrochemical imaging method according to a first aspect of the present invention, in the electrochemical imaging method for generating a plurality of images of density distributions of a plurality of measurement target substances which are generated or consumed by a sample in an electrolytic solution, comprising the steps of:

(a) providing a plurality of working electrodes arranged in a measurement area that faces the electrolytic solution, and a counter electrode placed in the electrolytic solution, the plurality of working electrodes comprises a plurality of working electrode groups each of which includes a plurality of working electrodes, the plurality of working electrodes included by each one of the plurality of working electrode groups, respectively, being arranged uniformly in the measurement area, such that the working electrodes included by all of the plurality of working electrode groups are mutually mixed in the measurement area;

(b) applying a voltage between each of the working electrodes included by all of the plurality of working electrode groups and the counter electrode, all simultaneously, and causing thereby the working electrode to perform a redox reaction that is one of giving electrons to and receiving electrons from one of the plurality of measurement target substances, the voltage is determined in accordance with the working electrode group that includes the working electrode;

(c) measuring a current that flows through each of the working electrodes included by all of the plurality of working electrode groups; and (d) generating an image of a density distribution in the measurement area of each of the plurality of measurement target substances based on a distribution in the measurement area of the measured currents that flow through the working electrodes included by one of the plurality of working electrode groups that corresponds to the measurement target substance;

any two working electrode groups among the plurality of working electrode groups are mutually different in at least any of the determined voltage, presence/absence of a molecular modification of an electrode surface and a species of the molecular modification; and based on the individual distributions of the currents in the measurement area in accordance with the working electrode groups, the plurality of images of density distributions of the plurality of measurement target substances are acquired by simultaneous measurements.

According to an electrochemical imaging method according to a second aspect of the present invention, in the electrochemical imaging method for generating a plurality of images of density distributions of a plurality of measurement target substances which are generated or consumed by a sample in an electrolytic solution, comprising the steps of:

(a) providing a plurality of working electrodes arranged in a measurement area that faces the electrolytic solution, and a counter electrode and a reference electrode both placed in the electrolytic solution,
  the plurality of working electrodes comprises a plurality of current measurement working electrodes and a plurality of potential measurement working electrodes, the plurality of current measurement working electrodes and the plurality of potential measurement working electrodes, respectively, being arranged uniformly in the measurement area, such that the current measurement working electrodes and the potential measurement working electrodes are mutually mixed in the measurement area;

(b) applying a voltage between each of the plurality of current measurement working electrodes and the counter electrode all simultaneously, and causing thereby the current measurement working electrode to perform a redox reaction that is one of giving electrons to and receiving electrons from a first substance, the first substance being one of the plurality of measurement target substances;

(c) measuring a current that flows through each of the plurality of current measurement working electrodes;

(d) at the same time as step (c), measuring a potential of each of the plurality of potential measurement working electrodes that is influenced by a second substance, with the reference electrode as a reference, the second substance being another one of the plurality of measurement target substances; and (e) generating both of an image of a density distribution in the measurement area of the first substance based on a distribution in the measurement area of the measured currents and an image of a density distribution in the measurement area of the second substance based on a distribution in the measurement area of the measured potentials.

According to an electrochemical measurement apparatus according to the first aspect of the present invention, in the electrochemical measurement apparatus comprising
  an electrolytic solution tank capable of containing an electrolytic solution and a sample that generates or consumes a plurality of measurement target substances in the electrolytic solution;
  a plurality of working electrodes arranged in a measurement area, the measurement area being provided on a bottom surface of the electrolytic solution tank,
  the plurality of working electrodes comprises a plurality of working electrode groups each of which includes a plurality of working electrodes, the plurality of working electrodes included by each one of the plurality of working electrode groups, respectively, being arranged uniformly in the measurement area, such that the working electrodes included by all of the plurality of working electrode groups are mutually mixed in the measurement area;
  a counter electrode provided in the electrolytic solution tank;
  a voltage applying portion having a function of applying a voltage between each of the working electrodes included by all of the plurality of working electrode groups and the counter electrode, all simultaneously, the voltage is determined in accordance with the working electrode group that includes the working electrode; and
  a current measuring portion configured to measure a current that flows between each of the working electrodes included by all of the plurality of working electrode groups and the counter electrode;
  any two working electrode groups among the plurality of working electrode groups are mutually different in at least any of the determined voltage, presence/absence of a molecular modification of an electrode surface and a species of the molecular modification; and
  a distribution in the measurement area of the currents that flow through the working electrodes included by each one of the plurality of working electrode groups is acquired.

According to an electrochemical measurement apparatus according to the second aspect of the present invention, in the electrochemical measurement apparatus comprising
  an electrolytic solution tank capable of containing an electrolytic solution and a sample that generates or consumes a plurality of measurement target substances in the electrolytic solution;
  a plurality of working electrodes arranged in a measurement area, the measurement area being provided on a bottom surface of the electrolytic solution tank,
  the plurality of working electrodes comprises a plurality of current measurement working electrodes and a plurality of potential measurement working electrodes, the plurality of current measurement working electrodes and the plurality of potential measurement working electrodes, respectively, being arranged uniformly in the measurement area, such that the current measurement working electrodes and the potential measurement electrodes are mutually mixed in the measurement area;
  a counter electrode and a reference electrode both provided in the electrolytic solution tank, a voltage applying portion;
  a voltage applying portion having a function of applying a voltage between each of the plurality of current measurement working electrodes and the counter electrode, all simultaneously;
  a current measuring portion configured to measure a current that flows between each of the plurality of current measurement working electrodes and the counter electrode; and
  a potential measuring portion configured to measure a voltage between each of the plurality of potential measurement working electrodes and the reference electrode;
  a distribution in the measurement area of the measured currents and a distribution in the measurement area of potentials of the plurality of potential measurement working electrodes are acquired.

According to a transducer according to the present invention, in the transducer configured to be used for electrochemical measurement of a plurality of measurement target substances generated or consumed by a sample, comprising:
  an LSI chip;
  an electrolytic solution tank which is capable of containing an electrolytic solution and the sample immersed in the electrolytic solution, the electrolytic solution tank being mounted on the LSI chip; and a plurality of electrodes of the LSI chip which are two-dimensionally arranged in a measurement area provided on a bottom surface of the electrolytic solution tank, the plurality of electrodes comprises a plurality of types of electrodes each of which includes a plurality of electrodes, the plurality of types of electrodes being mutually differentiated by being different in at least any of a size of an electrode surface, presence/absence of a molecular modification of the electrode surface, and a species of the molecular modification, and the plurality of electrodes included by each one type of electrodes, respectively, are arranged uniformly in the measurement area, such that the electrodes included by all of the plurality of types of electrodes are mutually mixed in the measurement area.

According to an electrochemical imaging method according to the present invention, it is possible to simultaneously acquire images of density distributions of a plurality of kinds of measurement target substances. Therefore, it is possible to perform simultaneous multi-item evaluation and contribute to clarification of correlation among evaluation items.

Further, the electrochemical measurement apparatus and the transducer according to the present invention are suitable for use for such electrochemical imaging.

BRIEF DESCRIPTION OF THE DRAWINGS

FIG. 6A is a diagram showing an optical image of nerve-like cell aggregates;

FIG. 6B is a diagram showing electrochemical images of the nerve-like cell aggregates shown in FIG. 6A;

FIG. 7A is a diagram for illustrating arrays of four working electrode groups;

FIG. 7B is a schematic diagram showing electrochemical measurement of dissolved oxygen;

FIG. 7C is a schematic diagram showing electrochemical measurement of dopamine;

FIG. 7D is a schematic diagram showing electrochemical measurement of glucose;

FIG. 7E is a schematic diagram showing electrochemical measurement of calcium ions;

DETAILED DESCRIPTION OF THE EMBODIMENTS

Figure 1C:
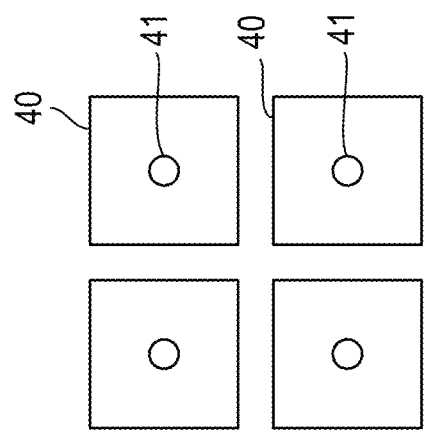
FIG. 1C is a diagram showing an array of cells of an LSI chip in FIG. 1A.

Embodiments of the present invention will be described below.

First, a configuration of a transducer used for electrochemical measurement of a measurement target substance generated or consumed by a sample will be described with reference to FIGS. 1A to 1D.

This transducer is called Bio-LSI and is configured such that an electrolytic solution tank 10 capable of containing an electrolytic solution 11 and a sample immersed in the electrolytic solution 11 is mounted on an LSI chip 20. A hole 12 is formed at the center of the electrolytic solution tank 10, and the LSI chip 20 is arranged under the bottom end of this hole 12 so as to cover the hole 12.

The LSI chip 20 and the electrolytic solution tank 10 are mounted and fixed on a board 30. On the board 30, a lot of wiring patterns 31 for connection with an external apparatus that acquires control and measurement data of the LSI chip 20 are formed. In FIG. 1B, reference numeral 32 denotes a bonding wire connecting the LSI chip 20 and the wiring patterns 31.

A measurement area 21 is configured on the top surface of the LSI chip 20. The measurement area 21 is shown with hatching in FIG. 1A, and the measurement area 21 is demarcated so as to face the electrolytic solution 11, at the position of the hole 12 on the bottom surface of the electrolytic solution tank 10.

Figure 1D:
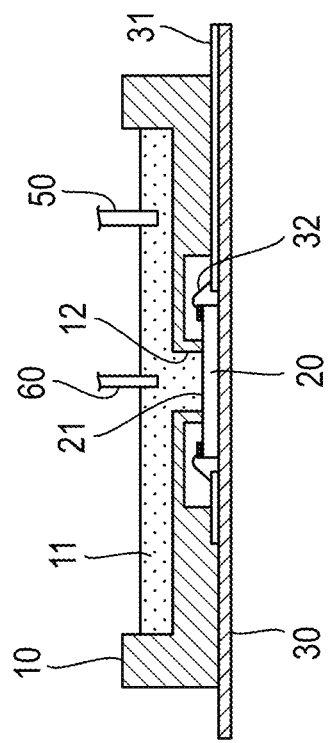
FIG. 1D is a diagram showing a working electrode provided in each cell.
Figure 1A:
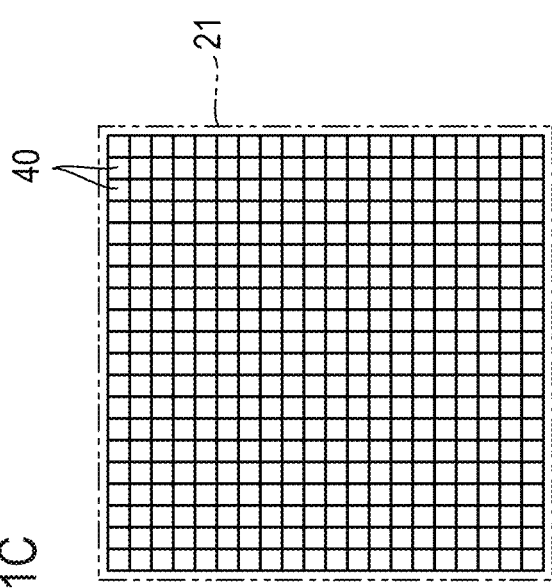
FIG. 1A is a plan view showing a configuration example of a transducer used for electrochemical measurement.
Figure 1B:
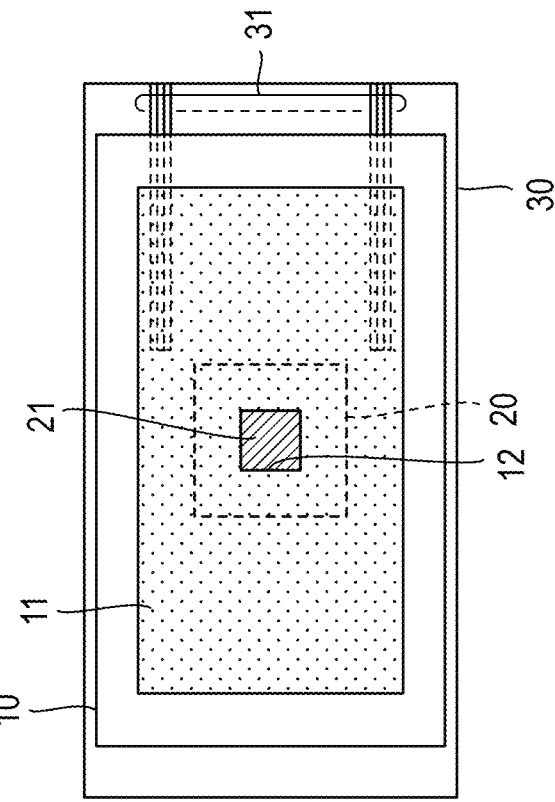
FIG. 1B is a cross-sectional view of the transducer shown in FIG. 1A.

In the measurement area 21, cells 40 are two-dimensionally arrayed and formed as shown in FIG. 1C. Each cell 40 is provided with a working electrode 41 as shown in FIG. 1D though it is not shown in FIG. 1C. In this example, the cells 40, the number of which is 20×20=400, are arranged and formed in an array at the pitch of 250 μm, that is, the LSI chip 20 has the working electrodes 41 the number of which is 20×20=400 and which are arranged in an array.

The LSI chip 20 is provided with a function of applying voltage to each working electrode 41, a function of detecting a reaction in each working electrode 41 as a current value and amplifying the current value and, furthermore, a switching function and the like. A counter electrode 50 and a reference electrode 60 required in electrochemical measurement are shown together in FIG. 1B, and the counter electrode 50 and the reference electrode 60 are placed in the electrolytic solution 11 as shown in FIG. 1B.

In the configuration as described above, it is assumed in the present invention that the working electrodes 41 are configured with a plurality of working electrode groups each of which comprises a plurality of working electrodes 41, and the working electrodes 41 are arranged in the measurement area 21 in a manner of being uniformly arranged in each working electrode group and in a manner of being mutually mixed.

Figure 2:
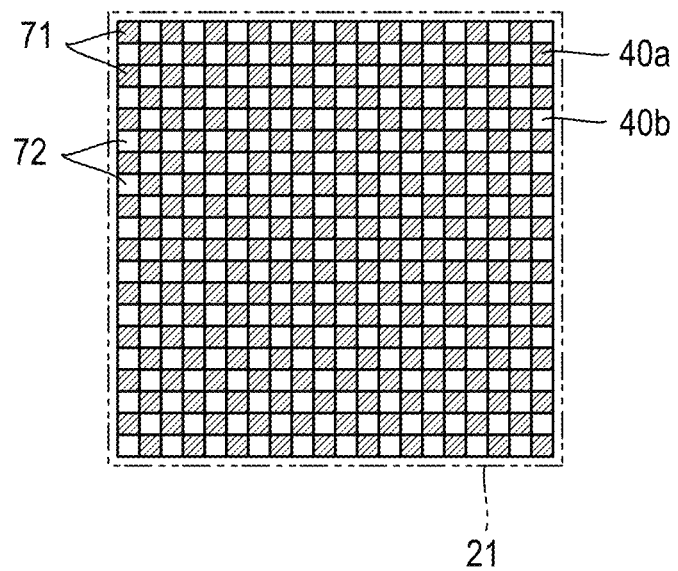
FIG. 2 is a diagram for illustrating arrays of two working electrode groups.

FIG. 2 shows positions of the working electrodes 41 in each working electrode group when the working electrodes 41 are configured with two working electrode groups on the LSI chip 20 shown in FIGS. 1A to 1D, by providing or not providing the cells 40 with hatching, without showing the working electrodes 41. Between two working electrode groups 71 and 72, working electrodes of the first working electrode group 71 are positioned in cells 40a with hatching and working electrodes of the second working electrode group 72 are positioned in cells 40b without hatching.

As shown in FIG. 2, the working electrodes of the first working electrode group 71 and the working electrodes of the second working electrode group 72 are arranged so as to be mutually alternately positioned in both of lines and rows, that is, in a checkered pattern. Thereby, the working electrodes are arranged in the measurement area 21 in a manner of uniformly arranged in each of the working electrode groups 71 and 72 and in a manner of being mutually mixed.

Voltages determined for the working electrode groups 71 and 72, respectively, are simultaneously applied to the working electrodes of the working electrode groups 71 and those of the second working electrode group 72. Here, for example, if different applied voltages are applied to the two working electrode groups 71 and 72, it becomes possible to simultaneously measure two kinds of measurement target substances.

Figure 3A:
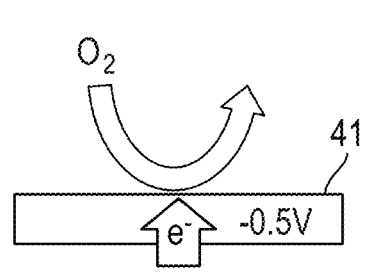
FIG. 3A is a schematic diagram showing electrochemical measurement of dissolved oxygen.
Figure 3B:
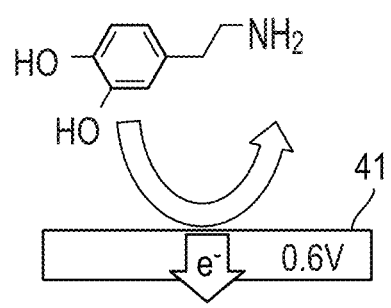
FIG. 3B is a schematic diagram showing electrochemical measurement of dopamine.

FIGS. 3A and 3B show an example of the two kinds of measurement target substances to be targeted by simultaneous measurement. The kinds of measurement target substances change according to voltage applied to the working electrodes 41. For example, if −0.5 V (vs. Ag/AgCl) is applied to the working electrodes 41 as shown in FIG. 3A, a reduction current of dissolved oxygen can be acquired. On the other hand, if 0.6 V (vs. Ag/AgCl) is applied to the working electrodes 41 as shown in FIG. 3B, an oxidation current of dopamine can be acquired.

By simultaneously measuring the reduction current of the dissolved oxygen and the oxidation current of the dopamine as described above, for example, a respiratory activity (an amount of oxygen consumed by cells) of nerve-like cells and release of a neurotransmitter can be simultaneously measured. That is, it is possible to measure change in a respiratory volume at the time when the nerve-like cells releases the neurotransmitter. Therefore, it becomes possible to non-invasively perform screening and analysis of the nerve-like cells.

Figure 4:
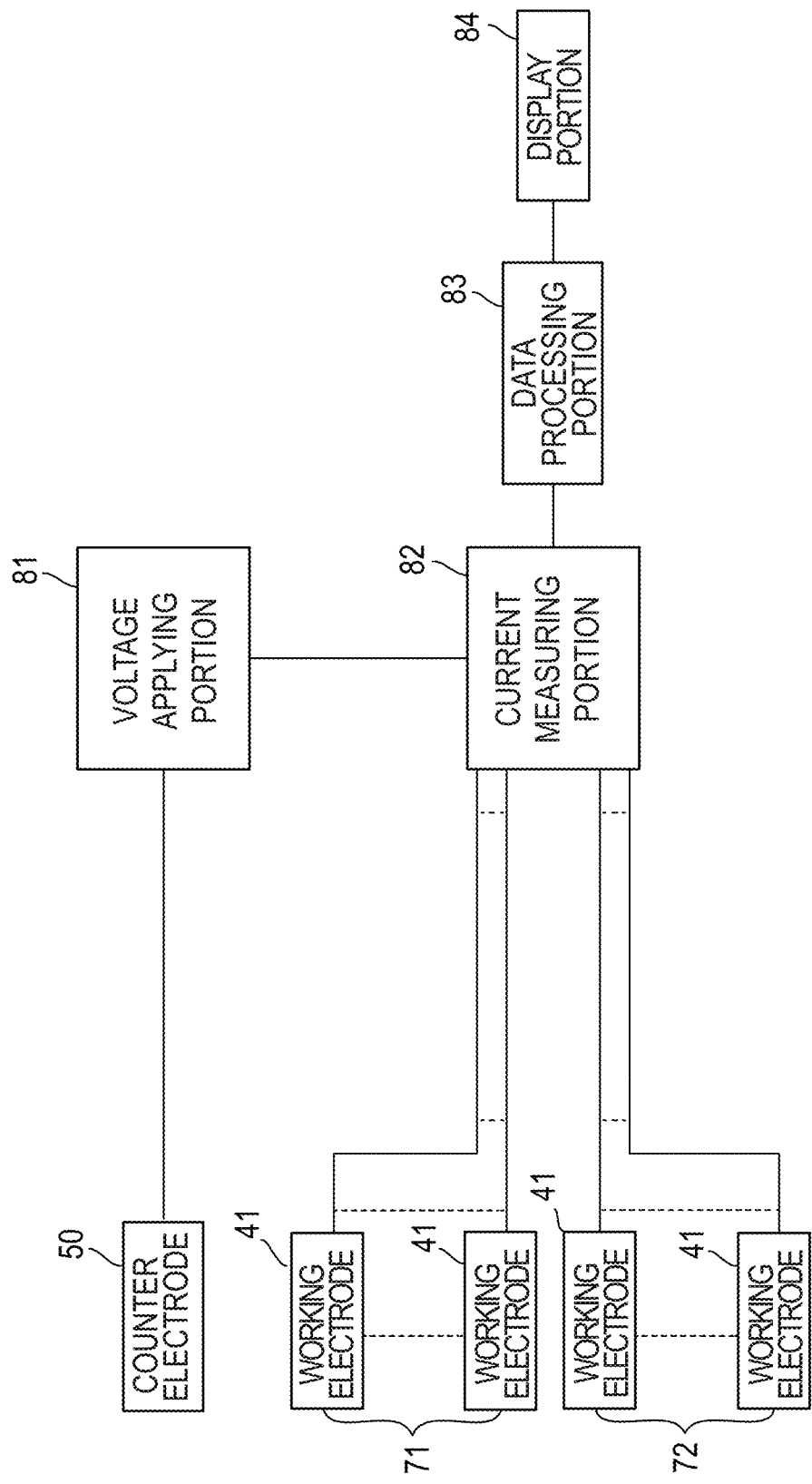
FIG. 4 is a block diagram showing an outline of a first embodiment of an electrochemical measurement apparatus according to the present invention.

FIG. 4 shows a functional configuration of an electrochemical measurement apparatus making it possible to simultaneously measure two kinds of measurement target substances as described above and perform imaging of the measurement target substances. This electrochemical measurement apparatus is configured comprising the transducer shown in FIGS. 1A to 1D. Furthermore, the working electrodes 41 are assumed to be configured with the two working electrode groups 71 and 72 as shown in FIG. 2.

A voltage applying portion 81 applies voltages between the working electrodes 41 and the counter electrode 50 and causes the working electrodes 41 to perform a redox reaction by giving and reception of electrons to and from measurement target substances. In this example, the voltage applying portion 81 simultaneously applies applied voltages determined for the working electrode group 71 and 72, respectively.

A current measuring portion 82 measures currents that flow between the working electrodes 41 and the counter electrode 50 by a redox reaction. In this example, the current measuring portion 82 measures distribution of the currents that flow through the working electrodes 41 in the measurement area 21, in each of the working electrode groups 71 and 72.

A data processing portion 83 has a function of performing data processing for interpolating data at a position where there is no working electrode 41, on the distribution of the currents that flow through the working electrodes 41 in the measurement area 21 in each of the working electrode groups 71 and 72 measured by the current measuring portion 82.

A display portion 84 overlappingly displays images of the distributions of the currents that flows through the working electrodes 41 in the measurement area 21 in the working electrode groups 71 and 72. In this example, the display portion 84 has a function of differentiating the images of the current distributions of the two working electrode groups 71 and 72 by colors and displaying a part where the two images overlap with each other by a color obtained by additively mixing the colors.

Figure 5A:
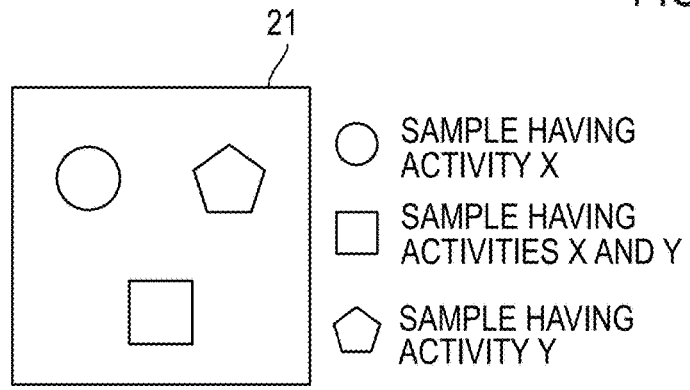
FIG. 5A is a diagram showing arrangement of samples with different activities.
Figure 5B:
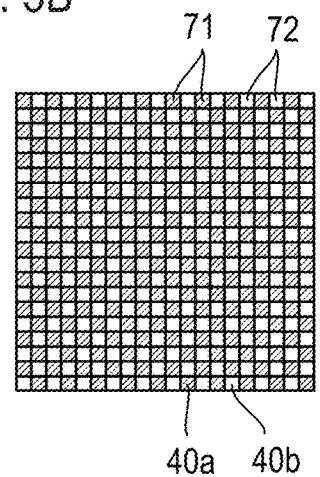
FIG. 5B is a diagram for illustrating applied voltages on working electrodes of the two working electrode groups.
Figure 5C:
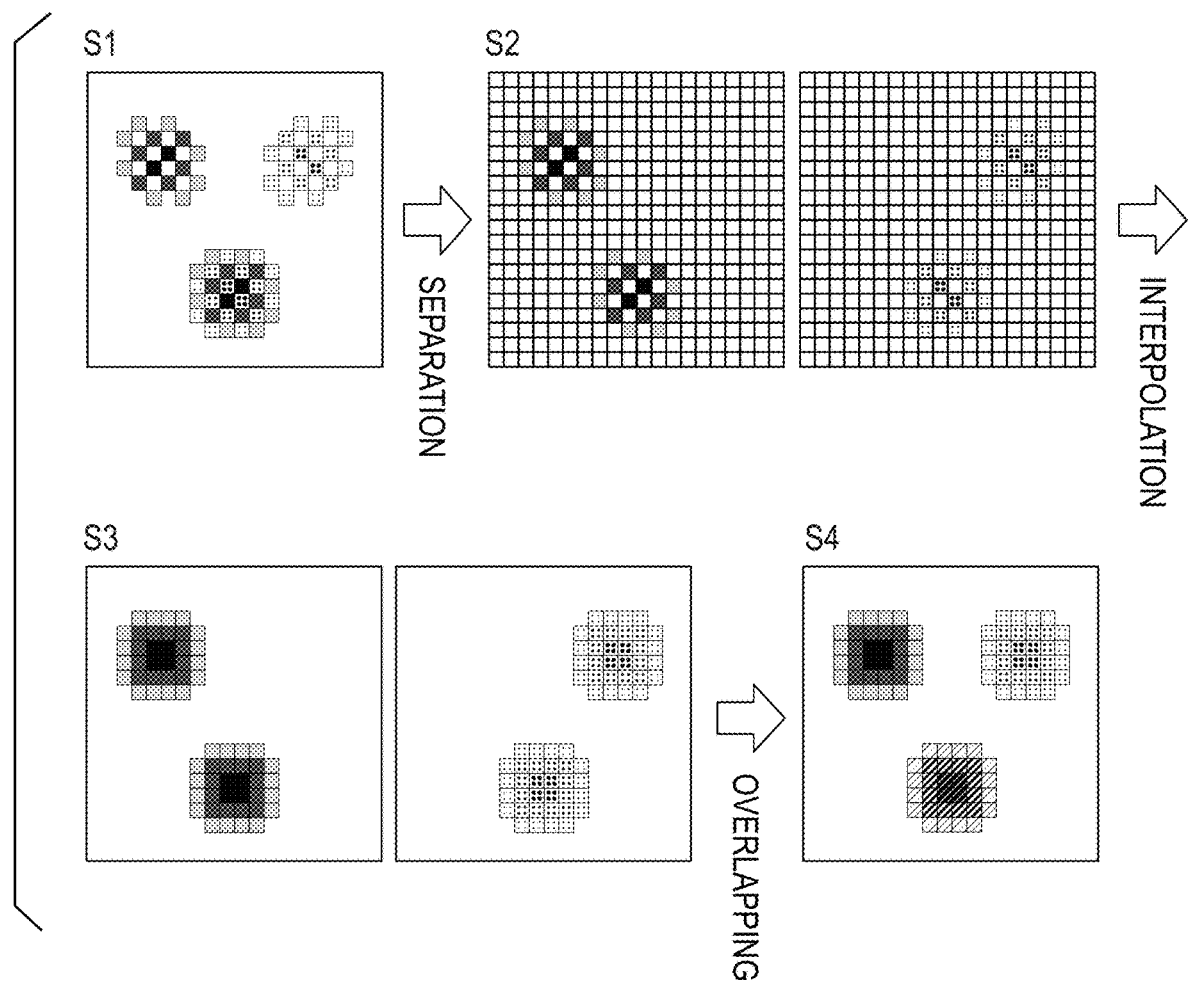
FIG. 5C is a diagram for illustrating an electrochemical imaging method according to the present invention.

FIGS. 5A to 5C schematically show a process of an electrochemical imaging method by the electrochemical measurement apparatus having the configuration as described above. The electrochemical imaging method will be described below in order with reference to FIGS. 5A to 5C.

It is assumed that an activity X and an activity Y are different activities and that a sample having the activity X, a sample having the activities X and Y, and a sample having the activity Y are arranged in the measurement area 21 as shown in FIG. 5A.

It is assumed that, similarly to FIG. 2 described before, the working electrodes 41 of the measurement area 21 are configured with the two working electrode groups 71 and 72 as shown in FIG. 5B. It is assumed that voltage for measuring the activity X is applied to the working electrodes of the working electrode group 71 indicated by the cells 40a with hatching and voltage for measuring the activity Y is applied to the working electrodes of the working electrode group 72 indicated by the cells 40b without hatching.

S1 of FIG. 5C shows an image of distributions of currents obtained by the two working electrode groups 71 and 72. In this example, images obtained by the two working electrode groups 71 and 72, respectively, are displayed being differentiated by colors, red and green. In FIG. 5C, shades of red are indicated by shades of black (gray scale), and shades of green are indicated by differences among the sizes of four points given in the cells 40b.

S2 of FIG. 5C shows that S1 has been separated into the images obtained by the two working electrode groups 71 and 72, respectively. S3 shows images in which data has been interpolated by data processing at positions where there is no working electrode. S4 shows a completed electrochemical image which has been obtained by overlapping the interpolated images with each other. Parts that are yellowed by additive mixture of red and green are indicated by shades of hatching.

Thus, according to the electrochemical measurement apparatus shown in FIG. 4, it is possible to electrochemically image two kinds of measurement target substances simultaneously, that is, it is possible to acquire an image of density distributions of the two kinds of measurement target substances.

FIG. 6B shows an example of actually performing electrochemical imaging of a respiratory activity and dopamine release of nerve-like cell aggregates simultaneously. The nerve-like cell (PC12 cell) aggregates were made by a hanging drop method. After the nerve-like cell aggregates were introduced into fertilized bovine egg respiratory volume measurement liquid ERAM-2 ([$K^+$]=100 mM) contained in the electrolytic solution tank 10 on the LSI chip 20, −0.5 V (vs. Ag/AgCl) and 0.6 V (vs. Ag/AgCl) were applied to the working electrodes of the working electrode groups 71 and 72, respectively, and simultaneously measured a respiratory activity and dopamine release.

FIG. 6A shows an optical image of the nerve-like cell aggregates, and FIG. 6B shows an electrochemical image of the nerve-like cell aggregates. The electrochemical image displayed in differentiating colors is shown by a method similar to the method in FIG. 5C described before. According to an overlap drawing in FIG. 6B, it is seen that simultaneous imaging of the respiratory activity and the dopamine release could be realized.

Description has been made on simultaneous measurement and imaging of two kinds of measurement target substances. However, the number of kinds of measurement target substances to be simultaneously measured is not limited to two. It is also possible to increase the number of kinds.

FIGS. 7B to 7E show an example of four kinds of measurement target substances targeted by simultaneous measurement. FIG. 7A shows positions of the working electrodes 41 of each working electrode group when the working electrodes 41 are configured with four working electrode groups, by differentiatingly displaying the cells 40, similarly to FIG. 2 described before.

FIGS. 7B and 7C show detection of dissolved oxygen and detection of dopamine similarly to FIGS. 3A and 3B described before.

FIG. 7D shows detection of glucose. Current measurement of glucose is performed by utilizing an oxidation reaction. The glucose itself, however, is not oxidized by the working electrodes 41. Detection of glucose can be performed by forming a glucose oxidase film on the working electrodes 41 as a modified film. The glucose changes to gluconolactone by an action of glucose oxidase which is an enzyme. At the same time, oxygen in the electrolytic solution changes to hydrogen peroxide. Therefore, by a reaction of the working electrodes 41 oxidizing the hydrogen peroxide generated in this process, the concentration of the glucose can be indirectly measured. To the working electrodes 41, 0.7 V (vs. Ag/AgCl) is applied.

FIG. 7E shows detection of calcium ions. This detection is performed by potential measurement (potentiometry). The potential measurement is a method of measuring an electrode potential under a state that the current is constant (zero or a constant current other than zero), and it is possible to detect a substance that influences the electrode potential. Further, it is possible to specifically measure a target substance by electrode modification. Calcium ions can be measured by the calcium ions being trapped on a $Ca^{2+}$ selective film formed on the working electrodes 41 and the potential of the working electrodes 41 changing by the trap of the calcium ions. That is, calcium ions can be detected not by current measurement but by measurement of the potential of working electrodes based on a reference electrode.

The simultaneous measurement of four kinds of measurement target substances shown in FIGS. 7B to 7E is useful for evaluation of activities and functions of cells. For example, it is possible to, in order to check suitability for transplantation about transplantation nerve cells as a sample, simultaneously perform all of evaluation of the level of activities of the cells and growth ability of the cells, with measured distribution amounts of oxygen and glucose related to a respiratory activity and a metabolism activity as indicators, evaluation of functions as nerve cells by the amount of released neurotransmitter (dopamine), and measurement of the amount of released calcium ions related to other various functions of the cells.

Molecular modification of the electrodes (working electrodes) as shown in FIGS. 7D and 7E can be selectively performed for an electrode using a spotter or a printer commercially available as a dedicated device. Further, it is also possible to apply voltage to a selected electrode to perform modification by an electrochemical method. According to this method, it is advantageous that modification is easily performed because of the minute electrode surface.

Working electrodes of each of four working electrode groups 71 to 74 to measure the four kinds of measurement target substances shown in FIGS. 7B to 7E are positioned as shown in FIG. 7A. That is, the working electrodes of the first working electrode group 71 to detect dissolved oxygen are positioned in the cells 40a with hatching, and the working electrodes of the second working electrode group 72 to detect dopamine are positioned in the cells 40b in white. Further, the working electrodes of the third working electrode group 73 to detect glucose are positioned in cells 40c in black, and the working electrodes of the fourth working electrode group 74 to detect calcium ions are positioned in dotted cells 40d.

As shown in FIG. 7A, configuration units (sets of working electrodes) each of which is configured comprising one working electrode of each of the four working electrode groups 71 to 74 and has a square surface shape are configured being cyclically arranged in both of lines and columns in the measurement area 21 in this example. Thereby, the working electrodes are arranged in the measurement area 21 in a manner of being arranged uniformly in each of the working electrode groups 71 to 74 and in a manner of being mutually mixed.

Figure 8:
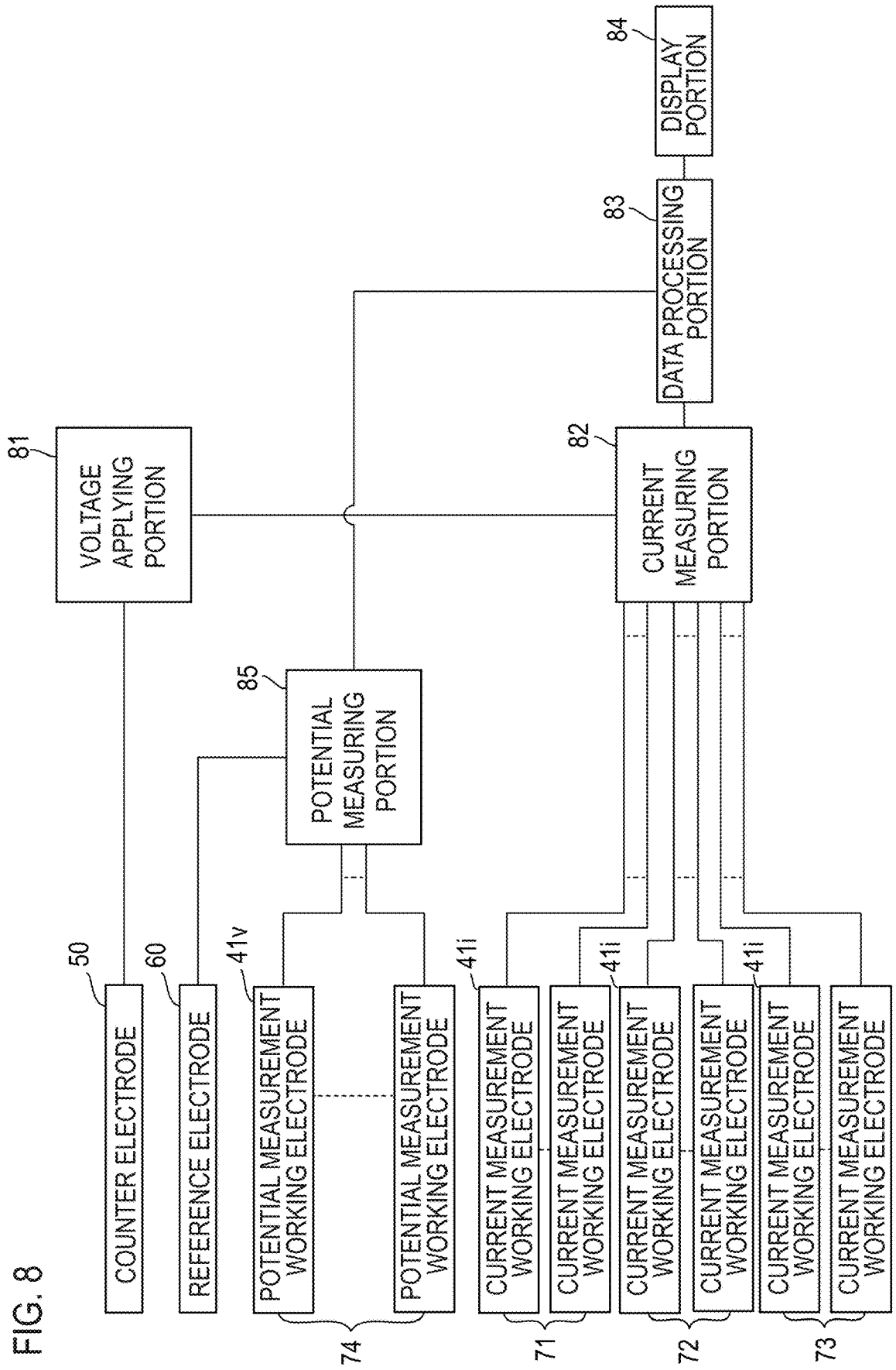
FIG. 8 is a block diagram showing an outline of a second embodiment of the electrochemical measurement apparatus according to the present invention.

FIG. 8 shows a functional configuration of an electrochemical measurement apparatus provided with the four working electrode groups 71 to 74 as described above and configured to simultaneously detect four kinds of measurement target substances and perform imaging of the measurement target substances. Parts corresponding to those of FIG. 4 are given the same reference numerals. In FIG. 8, the working electrodes 41 are shown being differentiated as current measurement working electrodes 41i and potential measurement working electrodes 41v.

The voltage applying portion 81 configured to apply voltages between the current measurement working electrodes 41i and the counter electrode 50 simultaneously apply applied voltages determined for the working electrode groups (current measurement working electrode groups) 71 to 73, respectively.

The current measuring portion 82 configured to measure currents that flow between the current measurement working electrodes 41$i$ and the counter electrode 50 measures distribution of currents that flow through the current measurement working electrodes 41$i$ in the measurement area 21 in each of the working electrode groups 71 to 73.

A potential measuring portion 85 measures distribution of potentials of potential measurement working electrodes 41$v$ of the working electrode group 74 in the measurement area 21.

The data processing portion 83 has a function of performing data processing for interpolating at least one of data for a position where there is no current measurement working electrode 41$i$, on the distribution of the currents that flow through the current measurement working electrodes 41$i$ in the measurement area 21 in each of the working electrode groups 71 to 73, which have been measured by the current measuring portion 82, and data for a position where there is no potential measurement working electrode 41$v$, on the distribution of the potentials of the potential measurement working electrodes 41$v$ of the working electrode group 74 in the measurement area 21, which have been measured by the potential measuring portion 85.

The display portion 84 overlappingly displays two or more images among images of the distributions of the currents that flow through the current measurement working electrodes 41$i$ in the measurement area 21 in the working electrode groups 71 to 73 and an image of the distribution of the potentials of the potential measurement working electrodes 41$v$ of the working electrode group 74 in the measurement area 21. The display portion 84 has a function of differentiating the two or more images by colors and displaying a part where the images overlap in a color obtained by additively mixing the colors.

According to the electrochemical measurement apparatus shown in FIG. 8, it is possible to electrochemically image a total of four kinds of measurement target substances, that is, three kinds of measurement target substances (first substances) detected by current measurement and one kind of measurement target substance (a second substance) detected by potential measurement at the same time.

Description has been made on an electrochemical measurement apparatus having two working electrode groups for current measurement and an electrochemical measurement apparatus having three working electrode groups for current measurement and one working electrode group for potential measurement. The number of working electrode groups that an electrochemical measurement apparatus has, however, is not limited to the above. The electrochemical measurement apparatus according to the present invention is characterized in having a plurality of working electrode groups.

It is assumed that, when a plurality of working electrode groups for current measurement are provided, any two of the plurality of working electrode groups are mutually different in at least any of applied voltages, presence/absence of molecular modification of working electrode surfaces, and the species of the molecular modification.

A configuration is also possible in which, in addition to working electrode groups for current measurement, a plurality of working electrode groups for potential measurement are provided. Furthermore, it is also possible to use only working electrodes for potential measurement as working electrodes, configure the working electrodes for potential measurement with a plurality of working electrode groups that are different in modification, and uniformly arrange working electrodes in each working electrode group so that a plurality of items are simultaneously measured in potential measurement, and imaging is performed.

The data processing portion 83 performs the data processing for interpolating data at a position where there is no working electrode. In a case where density of arrangement of working electrodes is sufficiently high, however, interpolation may not be performed. In this case, the display portion 84 displays an image for which interpolation has not been performed. Further, though the display portion 84 has the function of overlappingly displaying two or more images, the display portion 84 is also assumed to be capable of displaying images individually.

The size, number, arrangement and the like of working electrodes will be further described below.

It is assumed that working electrodes of each of the plurality of working electrode groups have a predetermined electrode area specified for the working electrode group. Further, in the examples described above, it is assumed that the working electrodes of all the working electrode groups have the same electrode area. However, at least two working electrode groups may have mutually different electrode areas.

Figure 9A:
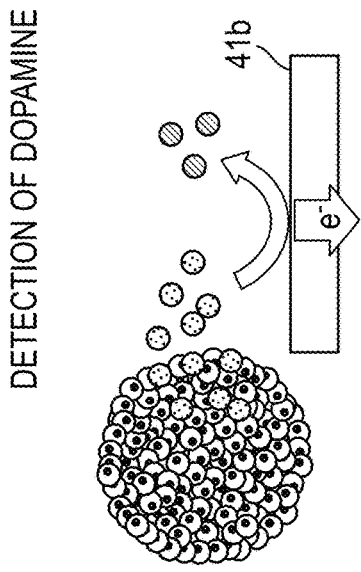
FIG. 9A is a diagram for illustrating arrays of two working electrode groups.
Figure 9B:
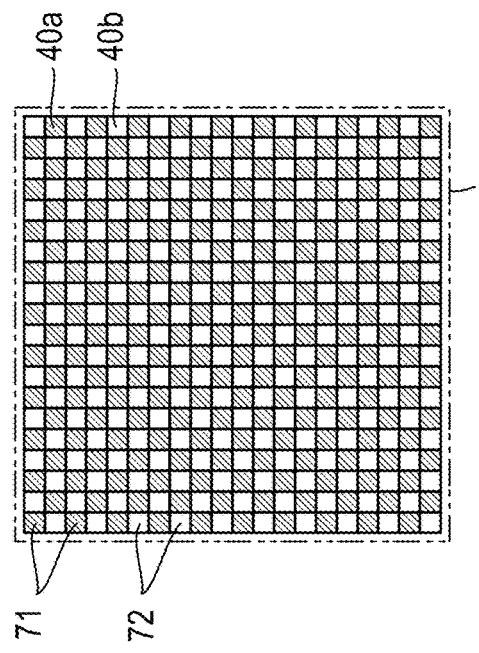
FIG. 9B is a diagram showing working electrodes of the two working electrode groups shown in FIG. 9A.

FIGS. 9A and 9B show an example in which working electrodes of two working electrode groups arranged in the measurement area 21 have different electrode areas according to the working electrode groups. FIG. 9A shows positions of the working electrodes of the two working electrode groups 71 and 72 similarly to FIG. 2. FIG. 9B shows working electrodes 41$a$ and 41$b$ provided in the cells 40$a$ and 40$b$ of the two working electrode groups 71 and 72 similarly to FIG. 1D.

In general, the smaller the electrode area (electrode size) is, the better the S/N (sensitivity) is. However, when the amount of measurement target substance is small, it is necessary to increase the electrode area in order to obtain a detectable current value. On the other hand, when the amount of measurement target substance is large, and a large current value can be secured, the electrode area may be small.

Figure 9C:
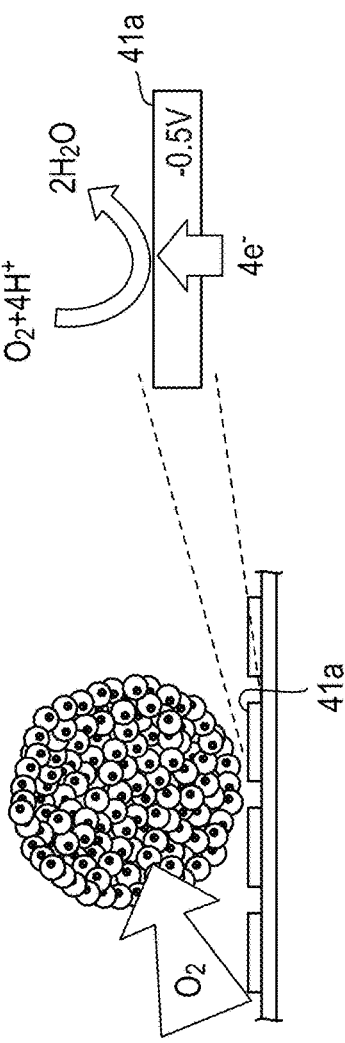
FIG. 9C is a schematic diagram showing a case where a working electrode with a large electrode area is suitable in electrochemical measurement.

FIG. 9C shows detection of dopamine as an example of the case where it is preferred to increase the electrode area as described above. When the amount of measurement target substance such as cell secretion is small, the electrode area is increased to increase the amount of substance to be caused to react on the electrode.

Figure 9D:
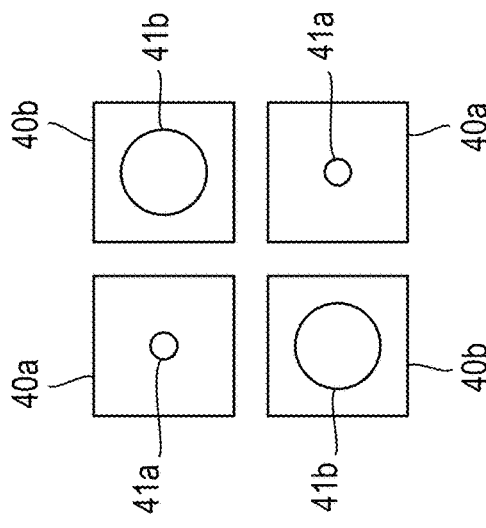
FIG. 9D is a schematic diagram showing a case where working electrodes with a small electrode area is suitable in electrochemical measurement.

On the other hand, for detection of dissolved oxygen, it is preferred that the electrode area is small as shown in FIG. 9D. Thereby, consumption of the measurement target substance is suppressed, and, therefore, it becomes possible to reduce the effect on the cells.

Next, the number (density) of working electrodes constituting each working electrode group will be described.

The working electrode densities of the working electrode groups are not necessarily required to be the same. It may be assumed that at least two working electrode groups among the plurality of working electrode groups are mutually different in the density of working electrodes arranged in the measurement area 21.

Figure 10:
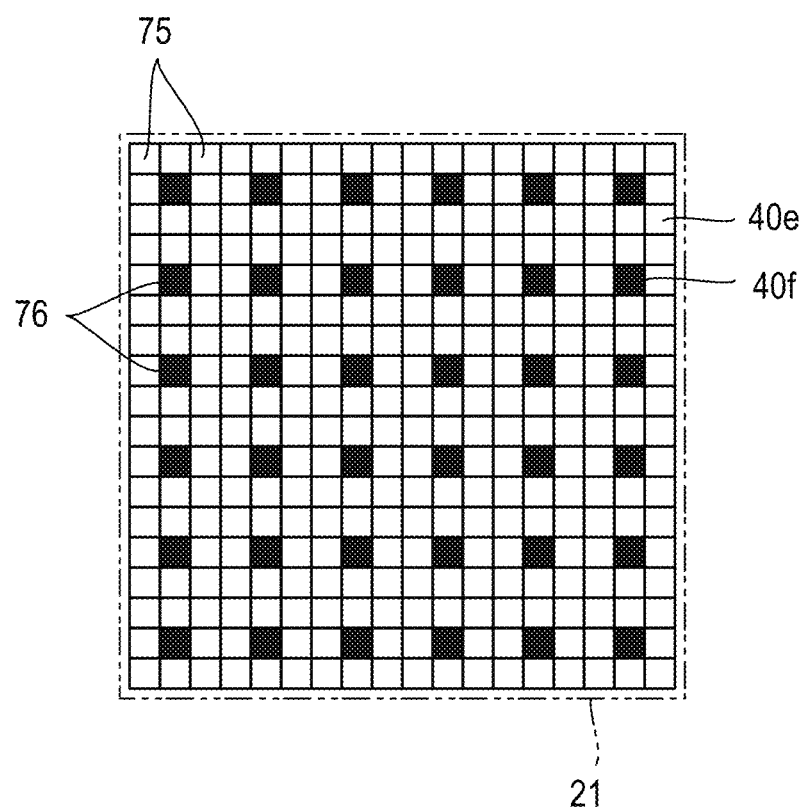
FIG. 10 is a diagram for illustrating arrays of two working electrode groups that are different in the number (density) of working electrodes.

FIG. 10 shows an example in which the working electrode densities of two working electrode groups arranged in the measurement area 21 are different. In FIG. 10, working electrodes of a working electrode group 75 are positioned in cells 40$e$ in white, and working electrodes of a working electrode group 76 are positioned in cells 40$f$ in black. The ratio of the number of working electrodes between the working electrode group 75 and the working electrode group 76 is 8:1.

When there are a lot of working electrodes as in the working electrode group 75, it becomes possible to acquire a high-resolution image. Therefore, this is suitable, for example, for the case of confirming a place where cell secretion is released. On the other hand, when there are few working electrodes as in the working electrode group 76, only a low-resolution image can be obtained, but the measurement area 21 can be used for measurement of other measurement target substances. For example, in the case of evaluating a respiratory activity of the whole cell aggregate, a low-resolution image is sufficient.

Next, arrangement of working electrodes of each working electrode group will be described.

Arrangement of the working electrodes of each working electrode group is only required to be uniform so that imaging is possible in the measurement area 21, and such uniform arrangement is typically realized by a cyclic arrangement. In all the examples described above, the configuration units of the working electrode array which are arranged cyclically are in a square surface shape. In general, however, any shape is possible if cyclic arrangement without space is possible.

Figure 11A:
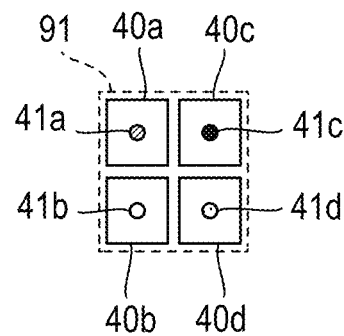
FIG. 11A is a diagram showing a configuration unit that comprises one working electrode of each of four working electrode groups.

FIG. 11A shows an example of a configuration unit configured having a set of working electrodes in a predetermined surface shape, the set of working electrodes being configured comprising one or more working electrodes specified for each of all the plurality of working electrode groups. In this example, a configuration unit 91 comprises one of working electrodes of each of four working electrode groups and has a square surface shape. In FIG. 11A, reference numerals 41a to 41d denote the working electrodes of the four working electrode groups, respectively.

Figure 11B:
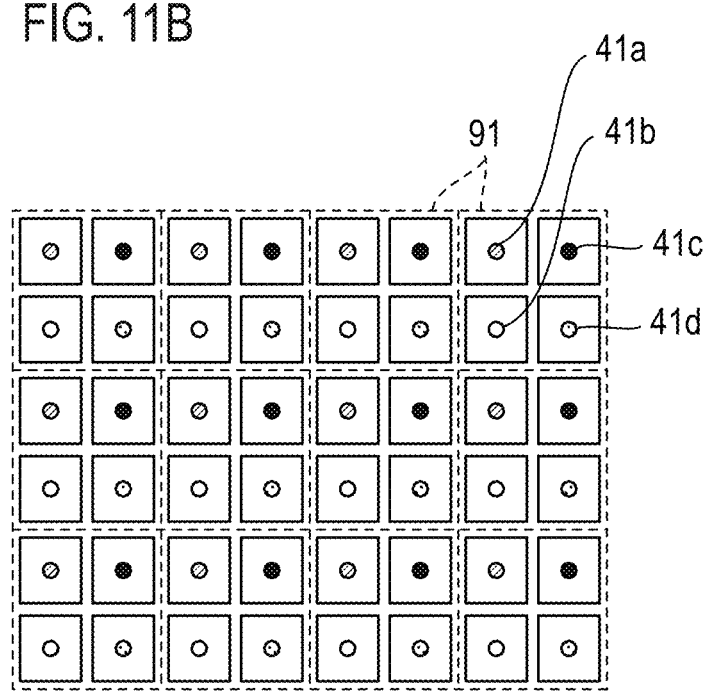
FIG. 11B is a diagram showing an example of an array of the configuration units shown in FIG. 11A.
Figure 11C:
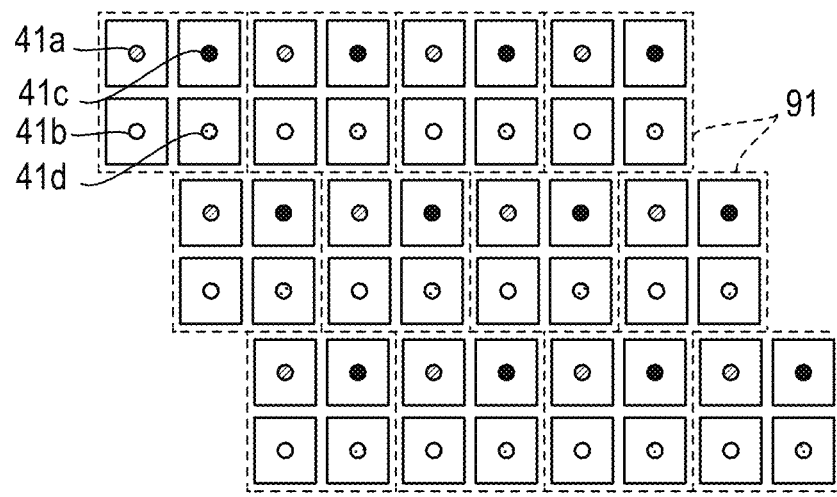
FIG. 11C is a diagram showing another example of the array of the configuration units shown in FIG. 11A.

FIG. 11B shows a state of the configuration units 91 being arranged in a matrix shape as an example of the configuration units 91 being cyclically arranged. Further, FIG. 11C shows a state in which lines on which the configuration units 91 are cyclically arranged are vertically arranged being displaced. The configuration units 91 are only required to be cyclically arranged without space and at least in one direction.

Figure 12A:
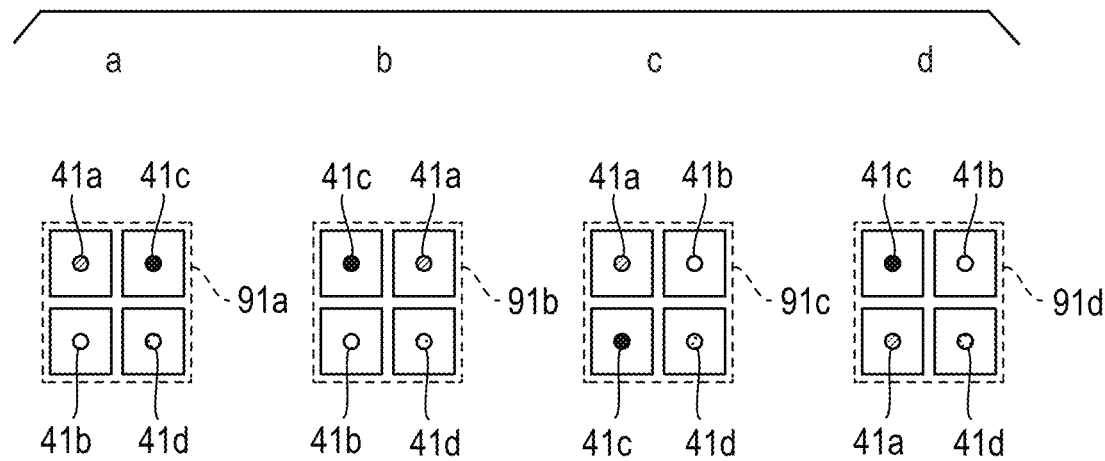
FIG. 12A is a diagram showing four arrangement patterns of the working electrodes in the configuration unit that comprises one working electrode of each of the four working electrode groups.
Figure 12B:
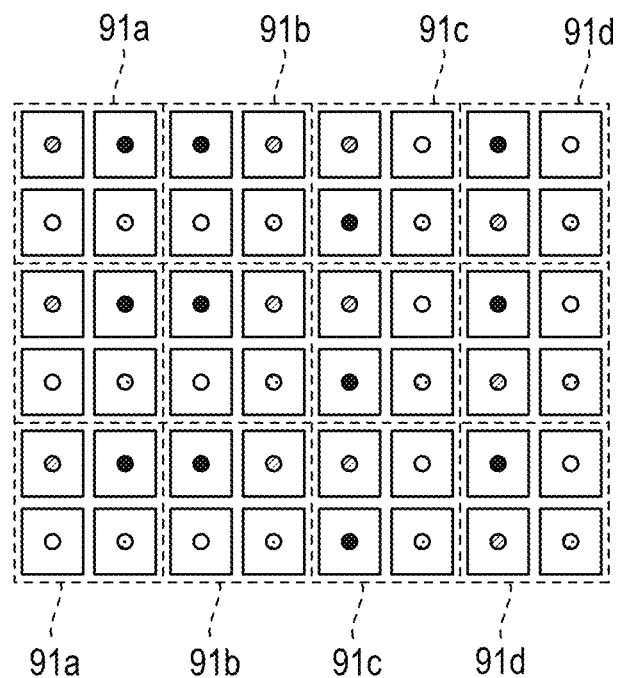
FIG. 12B is a diagram showing an example of an array of the four kinds of configuration units shown in FIG. 12A.

As long as a specified number of working electrodes, that is, the number of working electrodes specified for each working electrode group are comprised inside each configuration unit having a predetermined surface shape, uniformity in the whole measurement area 21 can be obtained. Therefore, how to arrange (the arrangement patterns of) the working electrodes inside the configuration units 91 may not be the same. For example, four configuration units 91a to 91d that are different in the arrangement pattern of the working electrodes 41a to 41d as shown in FIG. 12A (a) to FIG. 12A (d) may regularly exist in an array as shown in FIG. 12B or may irregularly exist. Furthermore, it is possible not only for the positions of working electrodes to be exchanged in the configuration unit but also for the positions of working electrodes to be more freely changed in the configuration unit.

It is assumed that, in the transducer according to the present invention, the plurality of working electrodes 41 are configured comprising a plurality of types of working electrodes that are mutually differentiated by being different in at least any of the sizes of the electrode surfaces, presence/absence of molecular modification of the electrode surfaces and the species of the molecular modification, the plurality of working electrodes are uniformly arranged in the measurement area 21 according to the types in a manner of being mutually mixed, in the configuration shown in FIGS. 1A to 1D. However, the arrangement of the working electrodes may be such as described with reference to FIGS. 11A to 11c and FIGS. 12A and 12B.

Various embodiments according to the invention have been described above. According to the electrochemical measurement method according to the present invention, it is possible to simultaneously acquire density distribution images of a plurality of kinds of measurement target substances. Therefore, it is possible to perform simultaneous multi-item analysis of a sample, and cell function analysis, cell evaluation, cell screening and the like become possible. Thereby, it is possible to significantly contribute to development of regenerative medicine, cell engineering and the like. Further, it is possible to expect application to evaluation of not only a biological sample but also battery material and catalyst material.

What is claimed is:

1. An electrochemical measurement apparatus comprising:
    an electrolytic solution tank capable of containing an electrolytic solution and a sample that generates or consumes a plurality of measurement target substances in the electrolytic solution;
    an array of working electrodes arranged in a measurement area provided on a bottom surface of the electrolytic solution tank, wherein the array of working electrodes comprises an array of current measurement working electrodes and an array of potential measurement working electrodes, the array of current measurement working electrodes and the array of potential measurement working electrodes, respectively, being arranged uniformly in the measurement area, such that the array of current measurement working electrodes spread in the measurement area and the array of potential measurement working electrodes spread in the measurement area are mixed in the measurement area;
    a counter electrode and a reference electrode both provided in the electrolytic solution tank;
    the apparatus adapted to apply a potential between each current measurement working electrode in the array of current measurement working electrodes and the counter electrode, all simultaneously;
    the apparatus adapted to measure a current that flows between each current measurement working electrode in the array of current measurement working electrodes and the counter electrode; and
    the apparatus adapted to measure a potential between each potential measurement working electrode in the array of potential measurement working electrodes and the reference electrode;
    whereby a distribution in the measurement area of the measured currents and a distribution in the measurement area of the measured potentials are acquired, wherein
        the array of current measurement working electrodes comprises a plurality of current measurement working electrode groups each including a plurality of current measurement working electrodes, the plurality of current measurement working electrodes included by each one of the plurality of current measurement working electrode groups, respectively, being arranged uniformly in the measurement area, such that the plurality of current measurement working electrodes included by any one of the plurality of current measurement working electrode groups, spread in the measurement area, and the plurality of current measurement working electrodes included by another one of the plurality of current measurement working electrode groups, spread in the measurement area, are mixed in the measurement area;

the apparatus adapted to apply the potential which is determined such that the potential applied to each of the plurality of current measurement working electrodes included by each group of the plurality of current measurement working electrode groups is the same;

any two current measurement working electrode groups among the plurality of current measurement working electrode groups are mutually different in at least any of the determined potential, the presence/absence of a molecular modification of an electrode surface, and a species of the molecular modification; and whereby the distribution in the measurement area of the measured currents that flow through the plurality of current measurement working electrodes included by each one of the plurality of current measurement working electrode groups is acquired, wherein each of the plurality of current measurement working electrodes included by each group of the plurality of current measurement working electrode groups has a same electrode area, and at least two of the current measurement working electrode groups have mutually different electrode areas.

2. An electrochemical measurement apparatus comprising:

an electrolytic solution tank capable of containing an electrolytic solution and a sample that generates or consumes a plurality of measurement target substances in the electrolytic solution;

an array of working electrodes arranged in a measurement area provided on a bottom surface of the electrolytic solution tank, wherein the array of working electrodes comprises an array of current measurement working electrodes and an array of potential measurement working electrodes, the array of current measurement working electrodes and the array of potential measurement working electrodes, respectively, being arranged uniformly in the measurement area, such that the array of current measurement working electrodes spread in the measurement area and the array of potential measurement working electrodes spread in the measurement area are mixed in the measurement area;

a counter electrode and a reference electrode both provided in the electrolytic solution tank;

the apparatus adapted to apply a potential between each current measurement working electrode in the array of current measurement working electrodes and the counter electrode, all simultaneously;

the apparatus adapted to measure a current that flows between each current measurement working electrode in the array of current measurement working electrodes and the counter electrode; and the apparatus adapted to measure a potential between each potential measurement working electrode in the array of potential measurement working electrodes and the reference electrode;

whereby a distribution in the measurement area of the measured currents and a distribution in the measurement area of the measured potentials are acquired, wherein the array of current measurement working electrodes comprises a plurality of current measurement working electrode groups each including a plurality of current measurement working electrodes, the plurality of current measurement working electrodes included by each one of the plurality of current measurement working electrode groups, respectively, being arranged uniformly in the measurement area, such that the plurality of current measurement working electrodes included by any one of the plurality of current measurement working electrode groups, spread in the measurement area, and the plurality of current measurement working electrodes included by another one of the plurality of current measurement working electrode groups, spread in the measurement area, are mixed in the measurement area;

the apparatus adapted to apply the potential which is determined such that the potential applied to each of the plurality of current measurement working electrodes included by each group of the plurality of current measurement working electrode groups is the same;

any two current measurement working electrode groups among the plurality of current measurement working electrode groups are mutually different in at least any of the determined potential, the presence/absence of a molecular modification of an electrode surface and a species of the molecular modification; and whereby the distribution in the measurement area of the measured currents that flow through the plurality of current measurement working electrodes included by each one of the plurality of current measurement working electrode groups is acquired, the apparatus further comprising a data processing portion configured to interpolate at least one of the acquired distribution of the measured currents at a position where a current signal from any current measurement working electrode in the array of current measurement working electrodes does not exist and the acquired distribution of the measured potentials at a position where a potential signal from any potential measurement working electrode in the array of potential measurement working electrodes does not exist.

3. A transducer configured to be used for electrochemical measurement of a plurality of measurement target substances generated or consumed by a sample, the transducer comprising:

an LSI chip;

an electrolytic solution tank which is capable of containing an electrolytic solution and the sample immersed in the electrolytic solution, the electrolytic solution tank being mounted on the LSI chip; and an array of electrodes of the LSI chip which are two-dimensionally arranged in a measurement area provided on a bottom surface of the electrolytic solution tank, wherein the array of electrodes comprises a plurality of electrode groups, each electrode group including a plurality of electrodes, each of the plurality of electrode groups being mutually different from another in at least any of a size of an electrode surface, the presence/absence of a molecular modification of the electrode surface and a species of the molecular modification, and wherein the plurality of electrodes included by each one of the plurality of electrode groups, respectively, are arranged uniformly in the measurement area, such that the plurality of electrodes included by any one of the plurality of electrode groups, spread in the measurement area, and the plurality of electrodes included by another one of the plurality of electrode groups, spread in the measurement area, are mixed in the measurement area.

4. The transducer according to claim 3, wherein a plurality of configuration units are cyclically arranged on the measurement area, each configuration unit being defined as a determined closed plane figure having therein arranged a determined set of electrodes, the determined set of electrodes comprising all of a respectively determined number of electrode(s) included by each of the plurality of electrode groups, wherein the respectively determined number is a positive natural number determined in accordance respectively with each of the plurality of electrode groups.

5. The transducer according to claim 4, wherein all the configuration units have a same arrangement pattern of the determined set of electrodes.

6. An electrochemical measurement apparatus comprising:
- an electrolytic solution tank capable of containing an electrolytic solution and a sample that generates or consumes a plurality of measurement target substances in the electrolytic solution;
- an array of working electrodes arranged in a measurement area provided on a bottom surface of the electrolytic solution tank, wherein the array of working electrodes comprises an array of current measurement working electrodes and an array of potential measurement working electrodes, the array of current measurement working electrodes and the array of potential measurement working electrodes, respectively, being arranged uniformly in the measurement area, such that the array of current measurement working electrodes spread in the measurement area and the array of potential measurement working electrodes spread in the measurement area are mixed in the measurement area;
- a counter electrode and a reference electrode both provided in the electrolytic solution tank;
- the apparatus adapted to apply a potential between each current measurement working electrode in the array of current measurement working electrodes and the counter electrode, all simultaneously;
- the apparatus adapted to measure a current that flows between each current measurement working electrode in the array of current measurement working electrodes and the counter electrode; and
- the apparatus adapted to measure a potential between each potential measurement working electrode in the array of potential measurement working electrodes and the reference electrode;

whereby a distribution in the measurement area of the measured currents and a distribution in the measurement area of the measured potentials are acquired, wherein
- the array of current measurement working electrodes comprises a plurality of current measurement working electrode groups each including a plurality of current measurement working electrodes, the plurality of current measurement working electrodes included by each one of the plurality of current measurement working electrode groups, respectively, being arranged uniformly in the measurement area, such that the plurality of current measurement working electrodes included by any one of the plurality of current measurement working electrode groups, spread in the measurement area, and the plurality of current measurement working electrodes included by another one of the plurality of current measurement working electrode groups, spread in the measurement area, are mixed in the measurement area;
- the apparatus adapted to apply the potential which is determined such that the potential applied to each of the plurality of current measurement working electrodes included by each group of the plurality of current measurement working electrode groups is the same;
- any two current measurement working electrode groups among the plurality of current measurement working electrode groups are mutually different in either:
  - the presence/absence of a molecular modification of an electrode surface, or a species of the molecular modification; and whereby
- the distribution in the measurement area of the measured currents that flow through the plurality of current measurement working electrodes included by each one of the plurality of current measurement working electrode groups is acquired.

* * * * *